United States Patent [19]

Buckberg et al.

[11] Patent Number: 5,226,427
[45] Date of Patent: Jul. 13, 1993

[54] REMOVABLE STYLET FOR RETROGRADE CARDIOPLEGIA CATHETER AND METHODS FOR USE

[75] Inventors: Gerald D. Buckberg, Los Angeles, Calif.; James C. McRea; Robert J. Todd, both of Salt Lake City, Utah

[73] Assignee: Research Medical Inc., Midvale, Utah

[21] Appl. No.: 710,720

[22] Filed: Jun. 4, 1991

Related U.S. Application Data

[63] Continuation-in-part of Ser. No. 187,230, Apr. 28, 1988, Pat. No. 5,021,045.

[51] Int. Cl.⁵ .................................................. A61M 5/18
[52] U.S. Cl. .................................... 128/772; 604/170
[58] Field of Search .............................. 128/10, 11, 207.29, 128/657, 772; 604/95, 170, 280

[56] References Cited

U.S. PATENT DOCUMENTS

| | | | |
|---|---|---|---|
| 1,282,881 | 10/1918 | Landis . | |
| 2,164,926 | 7/1939 | Kleine | 604/170 |
| 2,538,215 | 1/1951 | Stack . | |
| 2,669,233 | 2/1954 | Friend . | |
| 3,678,959 | 7/1972 | Liposky | 137/625.11 |
| 3,726,269 | 4/1973 | Webster, Jr. . | |
| 3,766,924 | 10/1973 | Pidgeon . | |
| 3,859,985 | 1/1975 | Eckhart . | |
| 3,867,945 | 2/1975 | Long | 604/170 |
| 4,154,227 | 5/1979 | Krause et al. . | |
| 4,210,478 | 7/1980 | Shoney | 156/242 |
| 4,249,923 | 2/1981 | Walda | 62/394 |
| 4,284,073 | 8/1981 | Krause et al. . | |
| 4,351,341 | 9/1982 | Goldberg et al. . | |
| 4,397,335 | 8/1983 | Doblar et al. | 137/625.19 |
| 4,413,989 | 11/1983 | Schjeldahl et al. | 604/96 |
| 4,416,280 | 11/1983 | Carpenter et al. | 128/399 |
| 4,427,009 | 1/1984 | Wells et al. | 128/400 |
| 4,433,971 | 2/1984 | Lindsay et al. | 604/122 |
| 4,447,590 | 5/1984 | Szycher | 528/76 |
| 4,459,977 | 7/1984 | Pizon et al. . | |
| 4,493,697 | 1/1985 | Krause et al. | 604/50 |
| 4,512,163 | 4/1985 | Wells et al. | 62/394 |
| 4,512,762 | 4/1985 | Spears | 604/21 |
| 4,529,397 | 7/1985 | Hennemuth et al. | 604/4 |
| 4,529,400 | 7/1985 | Scholten | 128/657 |
| 4,531,935 | 7/1985 | Berryessa | 604/45 |
| 4,531,936 | 7/1985 | Gordon | 604/49 |
| 4,535,757 | 8/1985 | Webster, Jr. . | |
| 4,566,480 | 1/1986 | Parham | 137/271 |
| 4,568,330 | 2/1986 | Kujawaski et al. | 604/53 |
| 4,610,661 | 9/1986 | Possis et al. | 604/52 |
| 4,648,384 | 3/1987 | Schmukler . | |
| 4,668,215 | 5/1987 | Allgood | 604/30 |
| 4,689,041 | 8/1987 | Corday et al. | 604/53 |
| 4,714,460 | 12/1987 | Calderon | 604/28 |
| 4,753,637 | 6/1988 | Horneffer | 604/53 |
| 4,784,638 | 11/1988 | Ghajer et al. | 604/49 |
| 4,790,825 | 12/1988 | Bernstein et al. | 128/772 |
| 4,804,358 | 2/1989 | Karcher et al. | 600/17 |
| 4,808,158 | 2/1989 | Kreuzer et al. | 604/170 |
| 4,863,430 | 9/1989 | Klyce et al. | 604/170 |

FOREIGN PATENT DOCUMENTS

1249338 12/1987 European Pat. Off. .

OTHER PUBLICATIONS

USCI, "Cardiovascular Catheters and Accessories", 1967-1968, p. 41.

(List continued on next page.)

Primary Examiner—Stephen C. Pellegrino
Assistant Examiner—Ralph A. Lewis
Attorney, Agent, or Firm—Workman, Nydegger & Jensen

[57] ABSTRACT

This invention relates to a stylet for use with a retrograde cardioplegia catheter and its methods of use. The stylet includes a stylet rod, a handle on the proximal end of the stylet rod and a predetermined curve in the distal end of the stylet rod. The handle has a thumb rest on the proximal end and a one or two finger loops extending outward from the handle. An obturator is located on the distal end of the predetermined curve to impede blood flow through a tip of the cardioplegia catheter during insertion of the catheter. The invention also contemplates methods for using the stylet.

17 Claims, 5 Drawing Sheets

OTHER PUBLICATIONS

C. R. Bard, Inc. "Urological Instruments", Eighth Edition, 1940, p. 20.

Gerald D. Buckberg, M. D., "Retrograde Pulmonary Venous Pressure Measurement-Fact or Artifact?", *The Journal of Thoracic and Cardiovascular Surgery*, vol. 59, No. 3, pp. 393–406, Mar. 1970.

Gerald D. Buckberg, M.D., "Strategies and Logic of Cardioplegic Delivery to Prevent, Avoid, and Reverse Ischemic and Reperfusion Damage", *The Journal of Thoracic and Cardiovascular Surgery*, 1987, vol. 93, pp. 127–139.

Partington, article covering the background for the use of antegrade/retrograde cardioplegic in combination submitted to the journal of Thoracic and Cardiovascular Surgery, date unknown.

Richard M. Engelman, M.D., "Retrograde Continuous Warm Blood Cardioplegia", *Ann Thorac Surg*, 1991, vol. 51, pp. 180–181.

John W. Kirklin, M.D., et al., "Prevention of Myocardial Damage During Cardiac Operations", *The New England Journal of Medicine* Jul. 1979, vol. 301, No. 3, pp. 135–141.

Harold V. Liddle and Richard Berryessa, "Metabolic Management of the Myocardium During Cardiac Surgery", *Blades Surgical Diseases of the Chest*, Chapter 23, pp. 649–671, published date and publisher unknown.

Dwight C. McGoon, M.D., "Coronary Perfusion", *Journal of Thoracic and Cardiovascular Surgery*, vol. 70, No. 6, p. 1025, Dec. 1975.

Philippe Menasche, et al., "Retrograde Coronary Sinus Perfusion", *Roberts Textbook Myocardial Protection in Cardiac Surgery*, printed 1987, Chapter 15, pp. 251–262.

Philippe Menasche, M. D. et al., "Retrograde Coronary Sinus Perfusion: A Safe Alternative for Ensuring Cardioplegic Delivery in Aortic Valve Surgery", *The Annals of Thoracic Surgery*, vol. 34, No. 6, Dec. 1982, pp. 647–658.

Donald G. Mulder, et al., "Myocardial Protection During Aortic Valve Replacement", *The Annals of Thoracic Surgery*, vol. 21, No. 2, Feb. 1976, pp. 123–130.

D. Glenn Pennington, "Direct Coronary Ostial Perfusion", *Nyocardial Protection in Cardiac Surgery*, edited by Arthur J. Roberts, published by Marcel Dekker Corp., New York and Basel, 1067; pp. 229–250.

Charles C. Reed, Diane K. Clark, Chapter 19, "Cannulation", Chapter 23 Myocardial Protection, *Cardiopulmonary Perfusion*, Texas Medical Press, Inc., Houston, TX, 1975.

Tomas A. Salerno, M. D. et al., "How To Do It, Technique and Pitfalls of Retrograde Continuous Warm Blood Cardioplegia", from the *Division of Cardiovascular Surgery St. Michael's Hospital and the Sunnybrook Health Science Center*, University of Toronto, Toronto, Ontario, Canada, undated.

Tomas A. Salerno, M. D., "Retrograde Continous Warm Blood Cardioplegia: A New Concept in Myocardial Protection", *Ann Thorac Surg*, 1991, vol. 51, pp. 245–247.

Jorge Solorzano, M.D., et al., "Retrograde Coronary Sinus Perfusion for Myocardial Protection During Cardiopulmonary Bypass", *The Annals of Thoracic Surgery*, vol. 25, No. 3, Mar. 1978, pp. 201–208.

International Working Group on Coronary Sinus Interventions, Newsletter, vol. 1, No. 3, Oct. 1987.

Picture illustrating use of a myocardial cannula during surgery, Date and source unknown, (Possibly from Roberts test).

A sales description of Mayo cannula from the V. Mueller Co. catalog.

REMOVABLE STYLET FOR RETROGRADE CARDIOPLEGIA CATHETER AND METHODS FOR USE

RELATED APPLICATION

This application is a continuation-in-part application of U.S. patent application Ser. No. 07/187,230 filed Apr. 28, 1988, now U.S. Pat. No. 5,021,045, Jun. 4, 1991, entitled "Retrograde Venous Cardioplegia Catheters and Methods of Use and Manufacture" naming as inventors Gerald D. Buckberg, M. D. and Robert J. Todd and is incorporated by specific reference herein.

BACKGROUND

1. Field of the Invention

This invention relates to the field of surgery, and more particularly to a stylet and methods of use for facilitating the performance of surgical procedures involving the placement of retrograde cardioplegia catheters.

2. Background Art

Since the early days of cardiac surgery, it has been recognized that in order to provide the optimum surgical conditions when operating on the heart, it is necessary to interrupt the normal operation of the heart. For obvious reasons, an arrested, flaccid heart is preferred during a cardiac surgical procedure over a beating heart with blood flowing through it. Thus, in order to be able to efficiently perform cardiac surgery, it is often necessary to use cardiopulmonary-bypass techniques and to isolate the heart from its life-giving blood supply.

It has been found that many deaths occurring after cardiac surgery are due to acute cardiac failure. At first, it was believed that the heart was simply beyond repair and that the operation had failed to correct the problem. Later, it was discovered that many of these postoperative deaths were due to new, and often extensive, perioperative (during or within 24 hours after the surgical procedure) myocardial necrosis (death of the heart tissue). Furthermore, many patients who survived were found to have suffered myocardial necrosis to a significant degree, thereby resulting in low cardiac blood output.

It is now known that myocardial necrosis occurs because the energy supply or reserve of the cardiac muscle cells is inadequate to supply the needs of the heart. The availability of oxygen dramatically affects the cell's ability to satisfy these energy requirements. For example, anaerobic metabolism of glucose produces two (2) moles of adenosine triphosphate ("ATP") per mole of glucose (as well as harmful acid metabolites), whereas aerobic metabolism of glucose produces thirty-six (36) moles of ATP per mole of glucose. Therefore, one of the primary goals of myocardial preservation techniques during surgery is to reduce myocardial oxygen consumption.

Myocardial oxygen consumption is significantly reduced by stopping the electromechanical work of the heart. The oxygen demands of the beating empty heart at 37° C. are four to five times those of the arrested heart (i.e., 4–5 ml/100-gm/min compared with 1 ml/100-gm/min). Buckberg, G. D., "Strategies and Logic of Cardioplegic Delivery to Prevent, Avoid, and Reverse Ischemic and Reperfusion Damage," 93 *The Journal of Thoracic and Cardiovascular Surgery*, 127, 136 (January 1987) (hereinafter referred to as: Buckberg, "Strategies and Logic of Cardioplegic Delivery").

One technique developed for stopping the electromechanical activity of the heart involves halting the heart by infusing high potassium cardioplegic solution. Cardioplegia, which literally means "heart stop," may be administered in an antegrade manner (through arteries in the normal direction of blood flow), in a retrograde manner (through veins opposite the normal blood flow direction), or in a combination of retrograde and antegrade administration. Cardioplegic solutions, typically containing potassium, magnesium procaine, or a hypocalcemic solution, stop the heart by depolarizing cell membranes. Blood is then redirected around the heart through a series of venous return tubes and catheters.

To gain access to the heart so that cardioplegic solution may be infused, early techniques utilized a surgical procedure requiring dissection of both cavae, the placing of tourniquets around the cavae, and the performance to two artiotomies. This allowed the positioning in the coronary sinus of a cardioplegia catheter through an incision in the right atrium. The cardioplegia catheter was held in place by inflating a retention balloon which surrounded the distal tip of the cardioplegia catheter. When inflated, the balloon wedged against the walls of the coronary sinus. Cardioplegic solution was then infused into the heart until it stopped beating. This procedure was repeated several times until the surgery was completed.

One serious disadvantages to this procedure was that the diseased and damaged heart was exposed to even further trauma by the need to dissect both cavae for visual verification of the cardioplegia catheter placement.

To overcome the need for cavae dissection prior to the administration of cardioplegic solution, stylets were developed which could be placed within a cardioplegia catheter to manually guide the catheter in place in the coronary sinus. These stylets were inserted through a very small slit instead of the large wound required for visual verification. A stylet is a thin rigid rod with a rounded tip to prevent puncturing of the cardioplegia catheter during installation. A stylet is inserted into an empty lumen or passageway that extends along most of the length of the catheter. The large lumen the stylet during installation of the catheter. The use of a rigid stylet gives the normally soft and pliable catheter enough rigidity to be manipulated within the heart from a position outside of the heart.

After insertion of the catheter into the heart, the catheter is then simply secured in place with a purse string suture, and the stylet is withdrawn from the catheter. Cardioplegic solution is then infused into the heart halting its pumping action. Once securely positioned, the catheter remains in place for the duration of the operation.

Although the use of a stylet decreased the trauma to the heart by obviating the need for cavae dissection, its use posed other problems. The passage of the catheter through a small incision blocked the visual placement of the catheter in the coronary sinus. Surgeons using a stylet were now required to guess the location of the catheter by observing the reaction of the heart and the pressure of the cardioplegic solution passing through the catheter.

In addition, stylets have only small hubs, left over from the manufacturing of the stylet, on which to grip the stylet during placement. This small handle limits the tactile feedback necessary to determine the location of the catheter within the heart.

One additional problem encountered when using a stylet occurs as the catheter is being positioned with the stylet in the coronary sinus of the heart. Since the heart is not dissected, pressure may remain within the heart which tends to fill the retention balloon of the cardioplegia catheter prior to final placement. Most retention balloons are designed to be inflated by the flow of cardioplegic solution through the balloon. After passage through the balloon, the cardioplegic solution flows into the heart. Pressure from the heart, however, may cause pressurized blood to flow backwards through the tip of the catheter and fill the balloon from the heart side. Since the surgeon cannot see the position or condition of the balloon, the premature back-filling may mislead the surgeon as to the location of the catheter within the heart or may inextricably wedge the balloon in an undesirable location. Mislocation of the catheter can lead to hemorrhage and other deleterious effects.

BRIEF SUMMARY AND OBJECTS OF THE INVENTION

The present invention is directed to a removable stylet for use in a retrograde cardioplegia catheter. The stylet of the present invention includes a stylet rod with a predetermined curve at the distal end and a handle at the proximal end. The stylet rod is constructed of a substantially rigid material such that the stylet can be used to removably position the flexible retrograde cardioplegia catheter in the coronary sinus with minimal trauma to heart tissues. As used in this specification the words "substantially rigid" are defined to indicate an item which is rigid enough to maintain its preformed shape in the absence of a deforming force, and to impart its shape to a flexible cannula when inserted therein, but yet which is pliable enough to conform to a somewhat different shape when urged to do so by insertion into the coronary sinus of a patient, thus avoiding trauma to the patient.

The handle of the inventive stylet provides a thumb rest located on the proximal end and a finger loop extending outward from one side of the handle. The finger loop projects from the side of the handle in the same direction as the predetermined curve.

One preferred embodiment of the present invention provides for an additional finger loop projecting from the other side of the handle for additional control.

An obturator for blocking the reverse flow of blood from a pressurized heart is provided at the distal end of the predetermined curve. The obturator is of a sufficient diameter to impede the flow of blood through the tip of an infusion lumen in a cardioplegia catheter. Impedance of backflow from the heart prevents the inflatable balloon from inadvertently filling prematurely.

Accordingly, it is one object of the present invention to provide a stylet for use in retrograde cardioplegia which allows positive control of the position of the cardioplegia catheter when placing the cardioplegia catheter within the heart.

A further object of the present invention is to provide a stylet that indicates to a surgeon the position of the cardioplegia catheter without visual contact.

Yet another object of the present invention is to provide a stylet which is capable of blocking an infusion lumen of a cardioplegia catheter to prevent backflow of blood from back-filling an inflatable balloon.

Additional objects and advantages of the invention will be set forth in the description which follows, and in part will be obvious from the description, or may be learned by the practice of the invention. The objects and advantages of the invention may be realized and obtained by means of the instruments and combinations particularly pointed out in the appended claims.

BRIEF DESCRIPTION OF THE DRAWINGS

In order that the manner in which the above-recited and other advantages and objects of the invention are obtained, a more particular description of the invention briefly described above will be rendered by reference to specific embodiments thereof which are illustrated in the appended drawings. Understanding that these drawings depict only typical embodiments of the invention and are, therefore, not to be considered limiting of its scope, the invention will be described with additional specificity and detail through the use of the accompanying drawings in which.

DETAILED DESCRIPTION OF THE PREFERRED EMBODIMENTS

Figure 1:
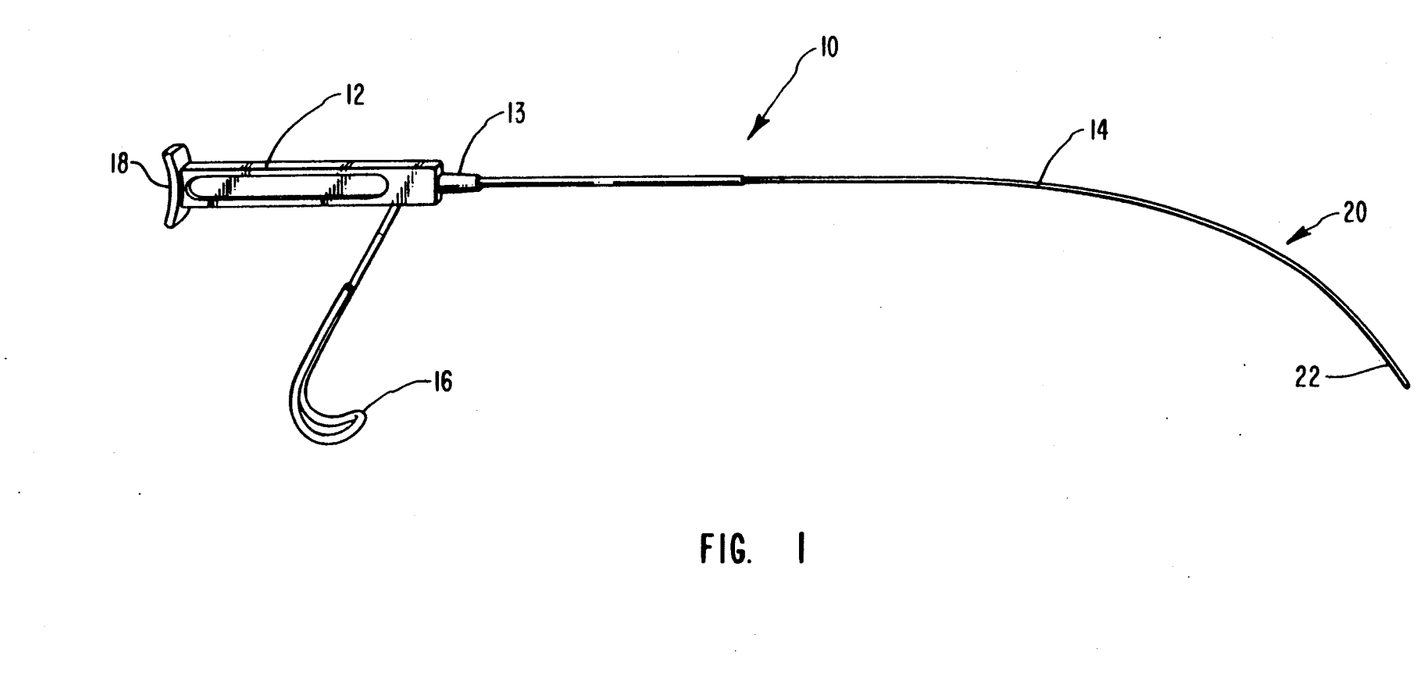
FIG. 1 is a perspective view of one presently preferred embodiment within the scope of the present invention.

FIG. 1 illustrates a presently preferred embodiment of the present invention. A stylet 10 provides a handle 12 which is located at a proximal end 13 of a stylet rod 14. A means for placement of a finger extending outwardly from handle 12 takes the form of a finger loop 16 which is used in conjunction with a thumb rest 18 to manipulate the stylet inside the body of a patient. Stylet rod 14 has a predetermined curve 20 at distal end 22 which aids in the proper placement of stylet 10 within the heart.

Figures 2, 3:
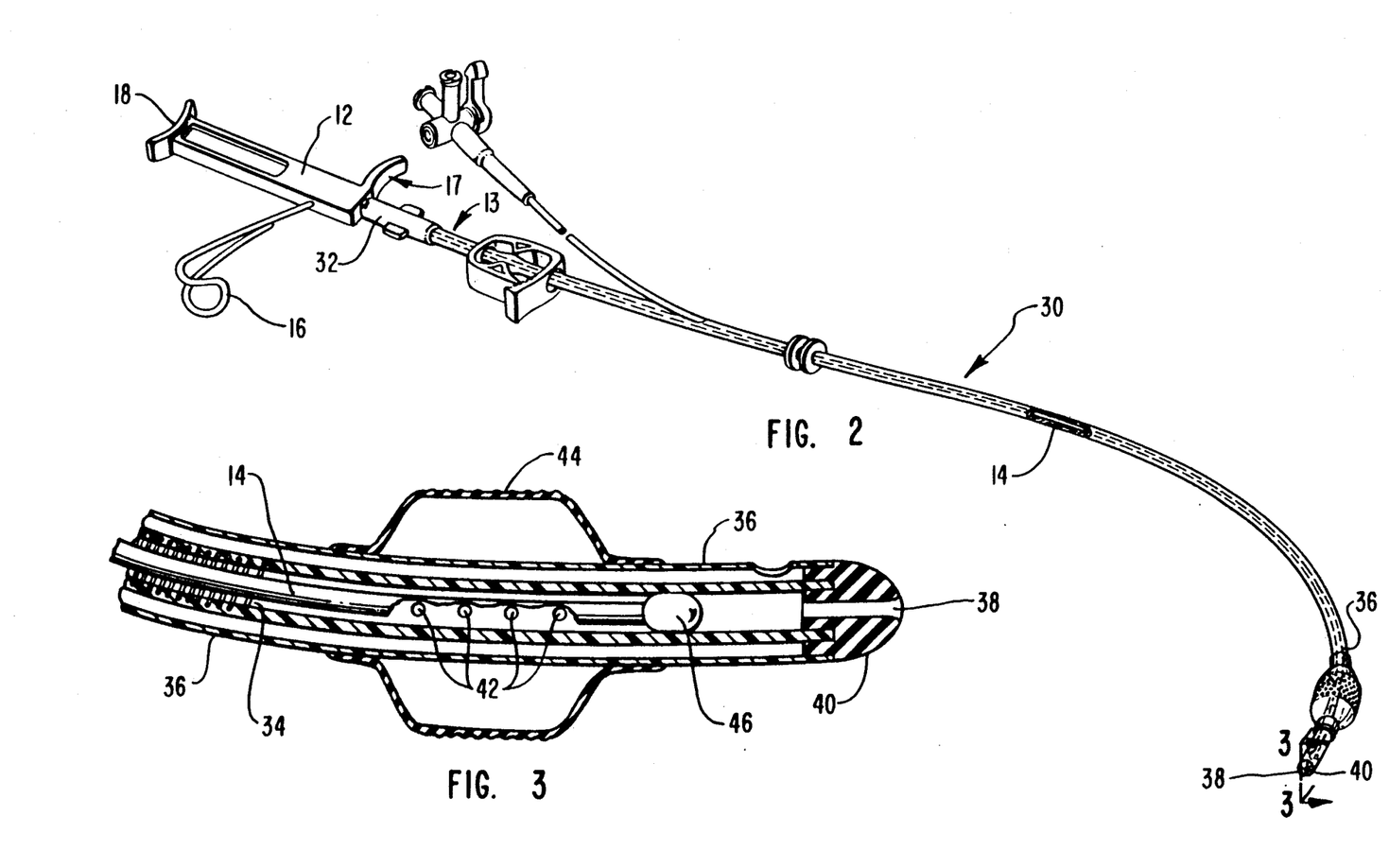
FIG. 2 is a perspective view of the present invention in the environment of its intended use.
FIG. 3 is a cross section of the retrograde cardioplegia catheter shown in FIG. 2 taken along line 3—3.

To best appreciate the environment in which the present invention finds its preferred use, FIG. 2 illustrates an inventive stylet inserted into a retrograde cardioplegia catheter 30. Stylet handle 12 can be seen protruding from proximal end 13 of catheter 30. A luer connector 32 stops handle 12 from being inserted further into catheter 30. The preferred embodiment illustrated in FIG. 2 also has an index finger loop 17 which extends outward from handle 12 in a direction opposite that of finger loop 16. Stylet rod 14 is shown extending along an infusion lumen 34 of catheter 30. Stylet rod 14 extends through infusion lumen 34 to distal end 36 of catheter 30. A portion of stylet rod 14 occludes an infusion lumen outlet 38 in a distal tip 40 of distal end 36.

The occlusion of infusion lumen outlet 38 is shown in greater detail in FIG. 3. In FIG. 3, infusion lumen 34 can be seen exiting at infusion lumen outlet 38. As cardioplegic solution passes along infusion lumen 34, some solution is diverted through a balloon orifice 42 to inflate an inflatable balloon 44 inside of the coronary sinus of a patient.

The inflation of balloon 44 wedges catheter 30 in place to prevent damage to the heart caused by movement of catheter 30. Although catheter 30 is manufactured of soft materials, the forward movement of catheter 30 after infusion has begun can lead to hemorrhage if the tip should perforate the coronary sinus. Therefore the tip is preferably configured so as to be particularly soft and pliant. Additionally, balloon 44 may be inflated prematurely by backflow from a pressurized heart. Blood in the pressurized heart may enter infusion lumen outlet 38 and fill balloon 44 through balloon orifices 42. To prevent such a premature inflation, the present invention provides an obturator 46 which is of sufficient diameter to impede the flow of blood through infusion lumen outlet 38 to prevent inflation of balloon 44. Obturator 46 may take the form of an elastomeric cup washer, elastomeric flange or a pliable bulb or many other forms which satisfy the teachings of the present invention. Obturator 46 must not be sufficiently large that removal will be difficult but must be sufficiently large to impede the flow of blood to prevent balloon 44 from inflating prematurely. To maintain the flexibility and softness of the tip of the catheter, obturator 46 does not extend to distal end 40 of catheter 30 but remains a distance back from end 40 between balloon 44 and infusion lumen outlet 38. When removable stylet 10 is withdrawn from infusion lumen 34 after proper positioning, catheter 30 is already in place and filling from back pressure will not impair the procedure.

It will be appreciated that the present invention overcomes the problem of premature filling of balloon 44 by blocking infusion lumen 34 and balloon orifices 42 from communication with the pressurized blood of the heart.

The present invention overcomes the problem of determining the orientation of the cardioplegia catheter within the heart by providing thumb rest 18 and finger loop 16, and optional loop 17. Through the use of thumb rest 18 and finger loops 16, 17, along with predetermined curve 20, a surgeon may determine from external indicia the orientation of catheter 30 within the heart.

In addition, handle 12 and its accompanying thumb rest 18 and finger loop 16, provides a large surface area with which to grip stylet 10. This large surface area provides for (shown only in FIGS. 2 and 6) tactile feedback and leverage unavailable with a small hub.

Figure 4:
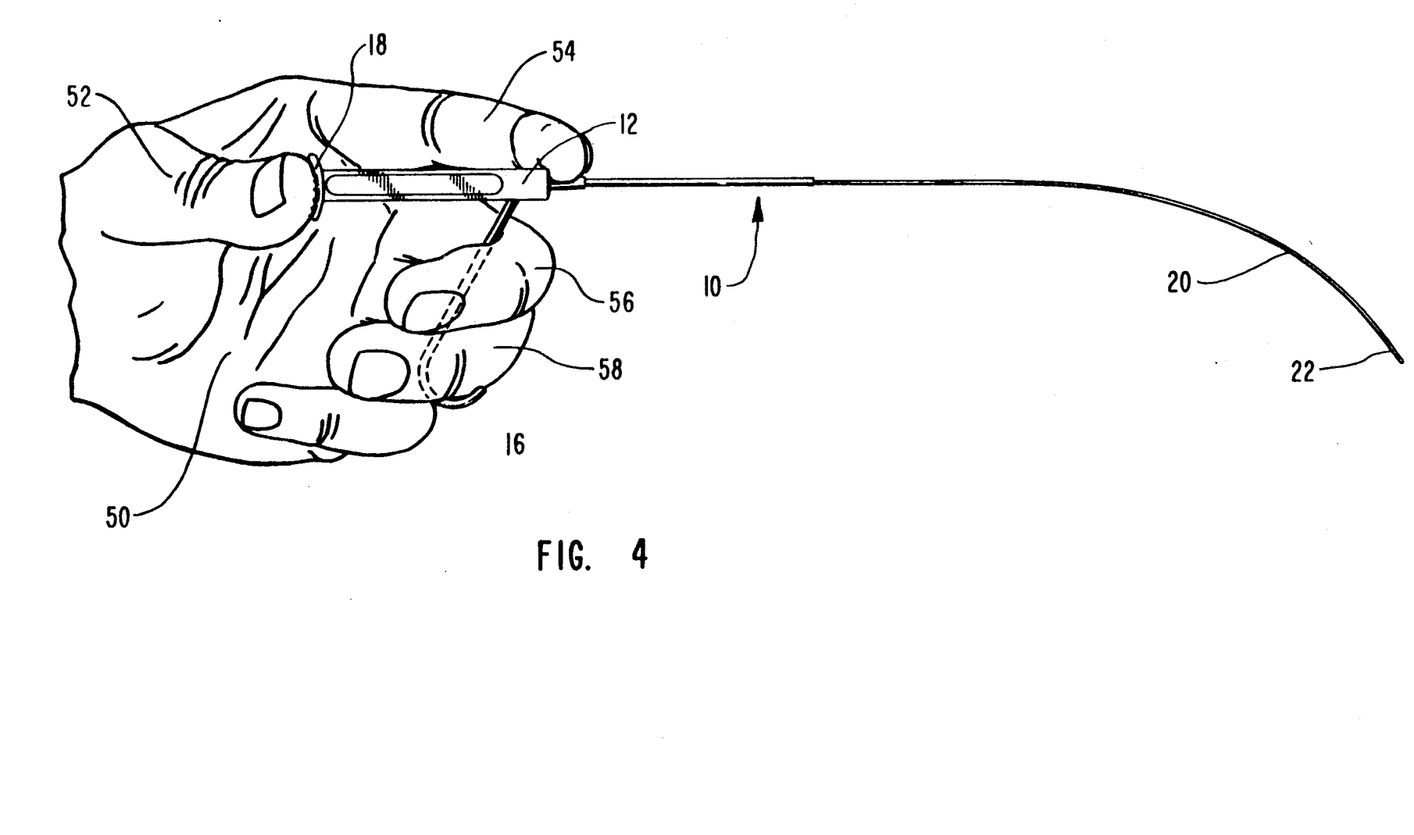
FIGS. 4, 5, and 6 illustrate the method of using the stylet.
Figure 5:
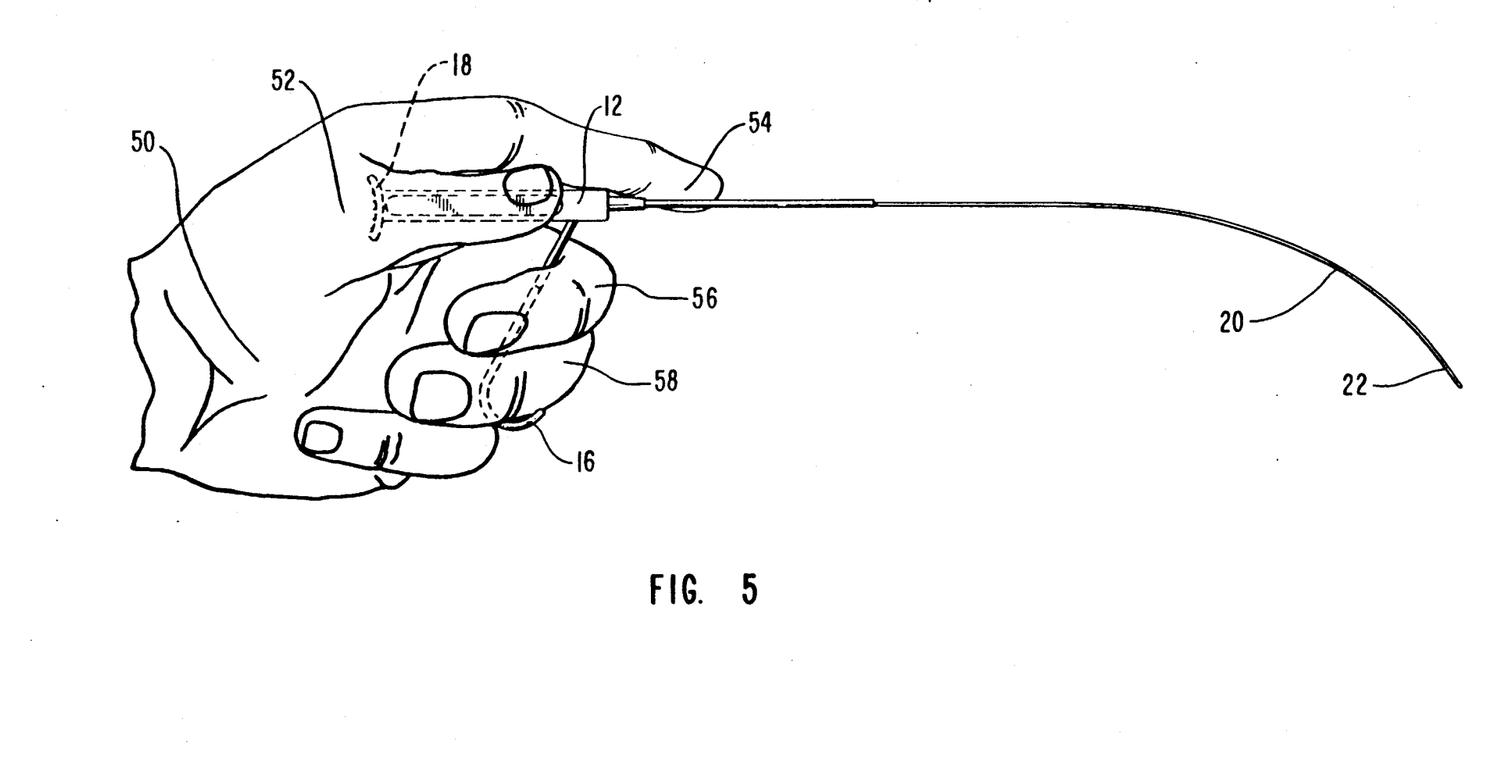
Figure 6:
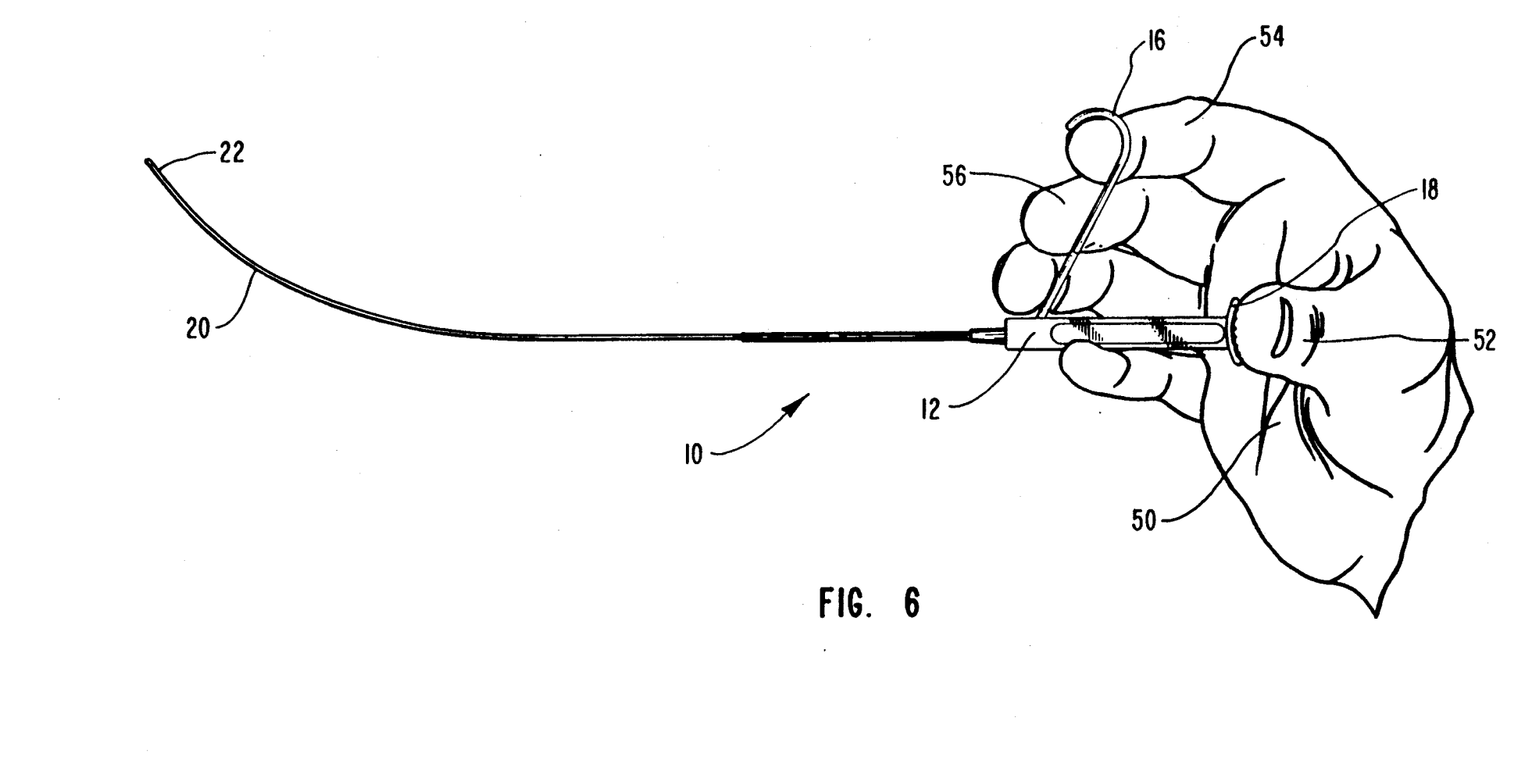

The steps comprising the method of using the stylet of the present invention are illustrated in FIGS. 4, 5 and 6.

FIG. 4 shows a left hand 50 of a surgeon gripping stylet 10. A thumb 52 is positioned on, and pressed against thumb rest 18. An index finger 54 is oriented substantially parallel to and pressed against handle 12 and a ring finger 58 is hooked around, and pressed against finger loop 16. With stylet 10 gripped in this manner, the retrograde cardioplegia catheter may be inserted within the coronary sinus of the patient by moving ring finger 58 toward the user while keeping thumb 52 and middle finger 56 relatively stationary.

It will be appreciated that the orientation of predetermined curve 20 relative to finger loop 16 appraises the surgeon of the location of distal end 22 even when distal end 22 is not visually perceptible to the surgeon. When desired, the free hand of the surgeon may be used to manipulate, or pulpate, the heart so that the coronary sinus is more easily accessible and to guide the cannula into place.

FIG. 5 shows left hand 50 utilizing a slightly different grip on stylet 10. Thumb 52 is placed substantially parallel to and pressed against handle 12 and index finger 54 is pressed against the top of the stylet. Thumb rest 18 is positioned in the crotch formed between index finger 54 and thumb 52. Ring finger 58 is hooked around, and pressed against finger loop 16 to give additional control.

With stylet 10 gripped in such a manner, the surgeon may simply insert a retrograde cardioplegia catheter within the coronary sinus of a patient by moving ring finger 58 toward the user while keeping thumb 52 and index finger 54 relatively stationary. The cannula will simply fall into place into the coronary sinus.

FIG. 6 shows a slightly different grip, employing an index finger loop 17.

It will be appreciated that the stylet described above may be used either with the right or left hand of the user depending on the user's preference and circumstances.

The curved stylet enables the catheter to be accurately positioned within the coronary sinus through such a small incision in the right atrium without visually seeing the coronary sinus. The unique stylet handle configuration gives the surgeon many options for holding the stylet and inserting the catheter within the coronary sinus. These options vary depending on the operating room condition, the position of the patient's heart, and the surgeon's own preference.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Patent is:

1. A removable stylet for use in a retrograde cardioplegia catheter during insertion of the retrograde cardioplegia catheter into the coronary sinus of the heart, the stylet comprising:
   (a) a stylet rod constructed of a substantially rigid material such that the stylet can impart the shape thereof upon a flexible cannula during insertion into the coronary sinus of a patient, the stylet rod having a predetermined curve at a distal end of the stylet body;
   (b) a handle located at the proximal end of the stylet rod, the handle comprising:
      (i) a handle body;
      (ii) thumb rest means located at a proximal end of the handle body for securely supporting the thumb of a user; and
      (iii) finger placement means, extending outwardly from a position on the handle body distal of the thumb rest means, for supporting at least one finger in order to allow manipulation of the stylet within the heart of a patient.

2. A removable stylet for use in a retrograde cardioplegia catheter as defined in claim 1, wherein the finger placement means comprises a substantially rigid wire formed into a loop.

3. A removable stylet for use in a retrograde cardioplegia catheter as defined in claim 2, wherein the loop extends outward from the handle in the same general direction as the predetermined curve.

4. A removable stylet for use in a retrograde cardioplegia catheter as defined in claim 3, wherein the loop is configured so as to support both the middle and ring fingers.

5. A removable stylet for use in a retrograde cardioplegia catheter as defined in claim 1, wherein the cardioplegia catheter with which the stylet is to be used includes an inflatable balloon, and wherein the stylet further comprises an obturator extending from a distal end of the predetermined curve, the obturator being of sufficient diameter to impede the flow of cardioplegic solution into the inflatable balloon of the cardioplegia catheter.

6. A removable stylet for use in a retrograde cardioplegia catheter as defined in claim 2, wherein the handle further comprises a second finger placement means, extending from the handle body on a side generally opposite the position on the handle body from which the loop extends, for supporting at least one other finger in order to facilitate manipulation of the stylet within the heart of a patient.

7. A removable stylet for use in a retrograde cardioplegia catheter during insertion of the retrograde cardioplegia catheter into the coronary sinus of the heart, the stylet comprising:
   (a) a stylet rod constructed of a substantially rigid material such that the stylet can impart the shape thereof upon a flexible cannula during insertion into the coronary sinus of a patient, the stylet rod having a predetermined curve at a distal end of the stylet body;
   (b) a handle located at the proximal end of the stylet rod, the handle comprising:
      (i) a handle body;
      (ii) a rigid thumb rest located on a proximal end of the handle body for securely supporting the thumb of a user; and
      (iii) a substantially rigid wire formed into a loop extending outwardly from a position on the handle body distal of the thumb rest means, for supporting at least one finger in order to allow manipulation of the stylet within the heart of a patient, the loop extending in a curve in the same general direction as the predetermined curve of the stylet rod; and
   (c) blocking means for obstructing the flow of blood located on the distal end of the stylet rod, the blocking means having a sufficient diameter to impede the flow of blood through a tip of a cardioplegia catheter.

8. A removable stylet for use in a retrograde cardioplegia catheter as defined in claim 7, wherein the cardioplegia catheter with which the stylet is to be used includes an inflatable balloon, and wherein the blocking means for obstructing the flow of blood is positioned on the stylet rod at a location so as to impede the backflow of blood from the heart before the blood reaches the inflatable balloon on the cardioplegia catheter.

9. A method of placing a retrograde cardioplegia catheter incorporating a stylet with a handle into the coronary sinus of a patient comprising the steps:
   (a) obtaining a removable stylet for use in a retrograde cardioplegia catheter during insertion of the catheter into the coronary sinus of the heart, the removable stylet comprising:
      (1) a stylet rod constructed of a substantially rigid material such that the stylet can impart the shape thereof upon a flexible cannula during insertion into the coronary sinus of a patient, the stylet rod having a predetermined curve at a distal end of the stylet body;
      (2) a handle located at the proximal end of the stylet rod, the handle comprising:
         (i) a handle body;
         (ii) thumb rest means, located at a proximal end of the handle body, for securely supporting the thumb of the user; and
         (iii) finger placement means, extending outwardly from a position on the handle body distal of the thumb rest means, for supporting at least one finger in order to allow manipulation of the stylet with in the heart of a patient;
   (b) pressing at least one finger of the user against the finger placement means of the handle of the stylet;
   (c) pressing a thumb of the user against the thumb rest means on the stylet handle; and
   (d) inserting the retrograde cardioplegia catheter within the coronary sinus of the patient through an incision permitting access to the coronary sinus with a slight movement of the at least one finger towards the user and keeping the thumb of the user relatively stationary.

10. A method of placing a retrograde cardioplegia catheter incorporating a stylet with a handle into the coronary sinus of a patient comprising the steps:
   (a) obtaining a removable stylet for use in a retrograde cardioplegia catheter during insertion of the catheter into the coronary sinus of the heart, the removable stylet comprising:
      (1) a stylet rod constructed of a substantially rigid material such that the stylet can impart the shape thereof upon a flexible cannula during insertion into the coronary sinus of a patient, the stylet rod having a predetermined curve at a distal end of the stylet body;
      (2) a handle located at the proximal end of the stylet rod, the handle comprising:
         (i) a handle body;
         (ii) thumb rest means, located at a proximal end of the handle body, for securely supporting the thumb of the user; and
         (iii) finger placement means, extending outwardly from a position on the handle body distal of the thumb rest means, for supporting at least one finger in order to allow manipulation of the stylet within the heart of a patient;
   (b) pressing an index finger of the user against a side of the stylet handle;
   (c) pressing a ring finger or the user against the finger placement means of the stylet handle;
   (d) pressing a thumb of the user against a side of the stylet handle, while impressing the thumb rest of the stylet handle in the crotch formed between the index finger and the thumb; and
   (e) inserting the retrograde cardioplegia catheter within the coronary sinus of the patient through an incision permitting access to the coronary sinus with a slight movement of the ring finger toward the user while keeping the thumb and index finger of the user relatively stationary.

11. A method of placing a retrograde cardioplegia catheter incorporating a stylet with a handle into the coronary sinus of a patient comprising the steps:
   (a) obtaining a removable stylet for use in a retrograde cardioplegia catheter during insertion of the catheter into the coronary sinus of the heart, the removable stylet comprising:
      (1) a stylet rod constructed of a substantially rigid material such that the stylet can impart the shape thereof upon a flexible cannula during insertion into the coronary sinus of a patient, the stylet rod having a predetermined curve at a distal end of the stylet body;

(2) a handle located at the proximal end of the stylet rod, the handle comprising:

(i) a handle body;

(ii) a thumb rest, located at a proximal end of the handle body, for supporting the thumb of the user;

(iii) a finger placement means, extending outwardly from a position on the handle body distal of the thumb, for supporting the ring finger in order to allow manipulation of the stylet within the heart of a patient;

(iii) a second finger placement means, extending outwardly from a position on the handle body distal of the thumb rest, for supporting the index finger in order to allow manipulation of the stylet within the heart of a patient; and (b) pressing an index finger of the user against the second finger placement means of the stylet;

(c) pressing the ring finger of the user against the first finger placement means of the stylet handle;

(d) pressing a thumb of the user against the thumb rest on the stylet handle; and (e) inserting the retrograde cardioplegia catheter within the coronary sinus of the patient through an incision permitting access to the coronary sinus with a slight movement of the ring finger toward the user and keeping the thumb and index finger of the user relatively stationary.

12. A removable stylet for use in a retrograde cardioplegia catheter during insertion of the retrograde cardioplegia catheter into the coronary sinus of the heart, the stylet comprising:

(a) a stylet rod constructed of a substantially rigid material such that the stylet can impart the shape thereof upon a flexible cannula during insertion into the coronary sinus of a patient, the stylet rod having a predetermined curve at a distal end of the stylet body;

(b) a handle located at the proximal end of the stylet rod, the handle having a surface area which allows tactile feedback and leverage during insertion of the catheter into the patient, the handle comprising:

(i) a handle body;

(ii) first support means, located at a proximal end of the handle body, for securely supporting a digit of a hand of a user so as to allow manipulation of the stylet within the heart of the patient, the first support means configured so as to securely support the digit in position; and (iii) second support means, extending outwardly from a position on the handle body distal of the first support means, for supporting at least one other digit of a hand of the user on the handle of the stylet in order to allow manipulation of the stylet within the heart of a patient.

13. A removable stylet for use in a retrograde cardioplegia catheter as defined in claim 1, wherein the second support means extends outward from the handle body in the same general direction as the predetermined curve at the distal end of the stylet body.

14. A removable stylet for use in a retrograde cardioplegia catheter as defined in claim 12, wherein the digit supported by the first support means is a thumb, and the at least one other digit supported by the second support means is a finger.

15. A removable stylet for use in a retrograde cardioplegia catheter as defined in claim 12, wherein the digit supported by the first support means is a finger, and the at least one other digit supported by the second support means is a thumb.

16. A removable stylet for use in a retrograde cardioplegia catheter as defined in claim 12, further comprising a third support means for supporting at least one other digit of the hand of a user.

17. A removable stylet for use in a retrograde cardioplegia catheter as defined in claim 12, wherein the stylet further comprises an obturator located on the distal end of the stylet rod of sufficient diameter to impede the flow of blood through a tip of the cardioplegia catheter.

* * * * *

UNITED STATES PATENT AND TRADEMARK OFFICE
CERTIFICATE OF CORRECTION

PATENT NO. : 5,226,427
DATED : July 13, 1993
INVENTOR(S) : GERALD D. BUCKBERG et al.

It is certified that error appears in the above-indentified patent and that said Letters Patent is hereby corrected as shown below:

```
    Title page, column 2 at Abstract, line 7, delete "a"
    Column 2, line 30, "disadvantages" should be --disadvantage--
    Column 2, line 45, after "lumen" insert --through which the
cardioplegic solution will pass often houses--
    Column 5, line 32, after "17" insert --(shown only in
Figures 2 and 6)--
    Column 5, line 40, delete "(shown only in FIGS. 2 and 6)"
    Column 5, line 47, after "against" insert --,--
    Column 5, line 60, "pulpate" should be --palpate--
```

Signed and Sealed this

Fifteenth Day of March, 1994

Attest:

BRUCE LEHMAN

*Attesting Officer*  *Commissioner of Patents and Trademarks*